United States Patent
Shiroyama et al.

(10) Patent No.: US 8,313,755 B2
(45) Date of Patent: Nov. 20, 2012

(54) CLEAR AQUEOUS CERAMIDE COMPOSITION

(75) Inventors: Kenichiro Shiroyama, Kanagawa (JP); Kenya Ishida, Kanagawa (JP); Hideaki Ohta, Kanagawa (JP); Toshimitsu Hagiwara, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/848,225

(22) Filed: May 4, 2001

(65) Prior Publication Data
US 2002/0010215 A1    Jan. 24, 2002

(30) Foreign Application Priority Data
May 11, 2000 (JP) .................................. 2000-138072

(51) Int. Cl.
*A61K 8/02* (2006.01)
*A01N 37/12* (2006.01)

(52) U.S. Cl. ........ 424/401; 514/551; 514/561; 514/844; 514/847

(58) Field of Classification Search ................. 424/70.1, 424/401, 70.11, 70.19, 70.22, 70.31
See application file for complete search history.

(56) References Cited

U.S. PATENT DOCUMENTS

| | | | |
|---|---|---|---|
| 4,992,266 A * | 2/1991 | Knoll .......................... | 424/70.11 |
| 5,294,444 A * | 3/1994 | Nakamura et al. ............. | 424/401 |
| 5,368,857 A | 11/1994 | Corcoran et al. ............. | 424/401 |
| 5,476,661 A * | 12/1995 | Pillai et al. .................... | 424/401 |
| 5,641,495 A * | 6/1997 | Jokura et al. .................. | 424/401 |
| 5,661,118 A * | 8/1997 | Cauwet et al. ................. | 510/126 |
| 5,773,611 A | 6/1998 | Zysman et al. | |
| 6,221,389 B1* | 4/2001 | Cannell et al. ................. | 424/450 |
| 6,348,601 B2* | 2/2002 | Ohlbach et al. ............... | 548/552 |
| 6,355,232 B1* | 3/2002 | Kaneko et al. ............... | 424/70.1 |

FOREIGN PATENT DOCUMENTS

| | | |
|---|---|---|
| EP | 0 790 053 A1 | 8/1997 |
| EP | 0875232 A1 | 11/1998 |
| EP | 0 920 852 A2 | 6/1999 |
| EP | 0875232 A1 | 11/1999 |
| JP | 63-192703 A | 8/1988 |
| JP | 3-8212 | 1/1991 |
| JP | 4-193814 A | 7/1992 |
| JP | 9-505065 | 5/1997 |
| JP | 9-315929 | 12/1997 |
| JP | 11-222416 A | 8/1999 |
| WO | WO 98/27958 | * 7/1998 |

OTHER PUBLICATIONS

Takagi, Y., et al., "Recent progress on the study of artificial ceramides especially regarding the barrier funciton of stratum corneum," Fragrance Journal, Japan, Oct. 15, 1999, vol. 27, No. 10, pp. 9-16.
European Patent Office, Office Action of Feb. 27, 2012, issued by the European Patent Office in corresponding European Application No. 01401179.5.
Database WPI Section Ch, Week 199650; Derwent Publication Ltd., London, GB; Class D13, AN 1996-500326 X002223933 & JP 08 256729 A (Nippon Oils & Fats Co Ltd), Oct. 8, 1996.
Data WPI Section Ch, Week 198343; Derwent Publication Ltd., London, GB; XP002223934 & JP 58 156330 A (Iatron Laboratories), Sep. 17, 1983.
European Office Action dated Nov. 7, 2008, issued by European Patent Office in corresponding EP Application No. 01 401 179.5.

* cited by examiner

*Primary Examiner* — Lakshmi Channavajjala
(74) *Attorney, Agent, or Firm* — Sughrue Mion, PLLC

(57) ABSTRACT

Provided is a clear aqueous ceramide composition comprising 1.0 to 5.0% by weight, based on the total composition, of a ceramide represented by formula (I):

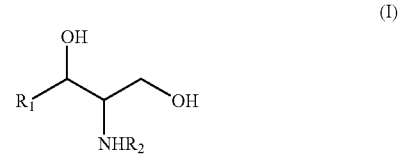

wherein $R_1$ represents a hydrocarbon group having 9 to 17 carbon atoms; and $R_2$ represents an acyl group having 2 to 30 carbon atoms which can contain a hydroxyl group, a long-chain fatty acid having 12 to 24 carbon atoms, a nonionic surface active agent, and water. The clear aqueous composition is useful as cosmetics, bath agents, hair-care products, external preparations for the skin, skin protective preparations, particularly medical external preparations for the treatment or protection of the skin, or a component making up these preparations.

19 Claims, No Drawings

CLEAR AQUEOUS CERAMIDE COMPOSITION

FIELD OF THE INVENTION

This invention relates to a clear aqueous ceramide composition, a method of preparing the same, applications comprising the ceramide composition, such as skin-care cosmetics, hair-care cosmetics and bath agents, and a lipid composition useful in the preparation of the clear aqueous ceramide composition.

BACKGROUND OF THE INVENTION

Skin performs very important functions as a barrier against the external environment, protecting from biological, chemical and physical attacks of microorganisms, chemical substances, ultraviolet rays, etc. and preventing loss of biologically essential components such as moisture. It is a stratum corneum having a thickness of about 20 μm, the outermost layer of the epidermis, that functions as the barrier. The stratum corneum is made up of flat corneous cells laid like bricks cemented with intercellular lipids. It is known that ceramides act as a key component of the intercellular lipids for making up the lipid barrier, playing an important role in keeping skin soft and fresh (see Downing D. T., et al., *J. Lipid Res.*, vol. 24, p. 759 (1983) and Dowing D. T., et al., *J. Invest. Dermat.*, vol. 84, p. 410 (1985)). It has been revealed that the skin of those suffering from rough skin, dry skin or atopic dermatitis has a noticeably reduced ceramide content in the intercellular lipids as compared with healthy skin. Attempts to improve skin conditions by supplementing rough skin with the intercellular lipids containing ceramides have been made. For example, external preparations containing ceramides or ceramide-containing intercellular lipids for application to the skin have been proposed.

However, ceramides are highly crystalline high-melting compounds and, because of their peculiar amphiphatic structure, have extremely low solubility in most of oil-soluble or water-soluble bases (solvents) for cosmetics. For this it has been difficult to formulate ceramides into stable preparations. That is, preparations having a high ceramide content easily undergo precipitation, or some lubricants which are used to dissolve a larger amount of a ceramide are unfavorable for safety.

It has recently been demanded to supply ceramides in the form of a clear solution for use in cosmetics or pharmaceuticals. To meet the demand JP-A-9-315929 (the term "JP-A" as used herein means an "unexamined published Japanese patent application") proposes a clear lipid composition comprising a sphingolipid, a lysophospholipid, and a polyhydric alcohol, the ratio of the sphingolipid to the lysophospholipid being 2/1 or less. This composition is a water-free mixture, however. JP-W-9-505065 (the term "JP-W" as used herein means a "world patent application (PCT) transfer originating from abroad") discloses a lipid composition in which a phytosphingosine-containing ceramide is stably suspended in a $C_6$-$C_{100}$ ester base and solubilized in a $C_8$-$C_{22}$ monofatty acid ester. It is desired for this composition to be free from water. In other words, the compositions of JP-A-9-315929 and JP-W-9-505065 have difficulty in keeping clear when mixed with water as is frequently used in formulation into final products, or in providing a clear preparation upon dilution with water to an arbitrary concentration.

Japanese Patent 3008212 teaches transparent or translucent cosmetics comprising (A) an amphiphatic lipid, (B) a nonionic surface active agent, (C) an ionic surface active agent, and (D) an aqueous medium, the ratio of (A) to [(B)+(C)] being 0.2 to 10. However, the amphiphatic lipids that are actually used are pseudoceramides. In addition, there is a fear of skin irritation due to the ionic surface active agent which is not preferred for cosmetics.

SUMMARY OF THE INVENTION

An object of the present invention is to provide an aqueous composition which contains a ceramide in a high concentration and yet shows excellent compatibility with water to secure clearness and stability and which has high safety, requiring no ionic surface active agents.

Another object of the invention is to provide a clear aqueous ceramide composition which can maintain clearness on dilution with water to an arbitrary concentration.

Still another object of the invention is to provide a clear aqueous ceramide composition which is ready for use in the preparation of cosmetics and pharmaceuticals excellent in stability, safety, and feel on application.

Yet another object of the invention is to provide a method of preparing the above-mentioned clear aqueous compositions.

A further object of the invention is to provide skin-care cosmetics, hair-care cosmetics and bath agents comprising the above-described clear aqueous composition.

A furthermore object of the invention is to provide a lipid composition which is useful to prepare the above-described clear aqueous ceramide compositions.

As a result of extensive investigation, the present inventors have found that a lipid composition comprising a ceramide, a long-chain fatty acid having 12 to 24 carbon atoms and a nonionic surface active agent exhibits high compatibility with water. Further researches based on this finding have successfully led them to obtain from the lipid composition a clear aqueous stable and safe composition which has a ceramide content of 1.0 to 5.0% by weight. The inventors have ascertained that the lipid composition and the clear aqueous composition can be diluted with water to an arbitrary concentration while keeping clear.

The present invention provides:

(1) A clear aqueous composition comprising (A) 1.0 to 5.0% by weight, based on the total composition, of a ceramide represented by formula (I):

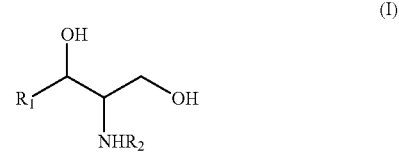

wherein $R_1$ represents a hydrocarbon group having 9 to 17 carbon atoms; and $R_2$ represents an acyl group having 2 to 30 carbon atoms which can contain a hydroxyl group, (B) a long-chain fatty acid having 12 to 24 carbon atoms, (C) a nonionic surface active agent, and (D) water.

(2) The clear aqueous composition as set forth in (1) above, wherein the ceramide represented by formula (I) is an optically active ceramide of natural type represented by formula (II):

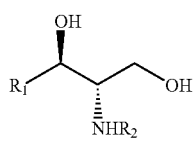

(II)

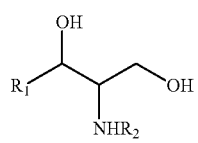

(I)

wherein $R_1$ and $R_2$ are as defined above.

(3) The clear aqueous composition as set forth in (1) or (2) above, wherein the long-chain fatty acid is at least one of isostearic acid and oleic acid.

(4) The clear aqueous composition as set forth in any one of (1) to (3), wherein the nonionic surface active agent is a polyoxyethylene hydrogenated castor oil.

(5) The clear aqueous composition as set forth in any one of (1) to (4) above, which further comprises at least one compound selected from the group consisting of a sterol compound and a polyhydric alcohol.

(6) The clear aqueous composition as set forth in (5) above, wherein the sterol compound is cholesterol.

(7) A method of preparing a clear aqueous composition comprising 1.0 to 5.0% by weight of a ceramide represented by formula (I):

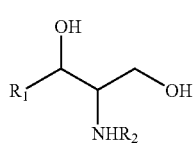

(I)

wherein $R_1$ represents a hydrocarbon group having 9 to 17 carbon atoms; and $R_2$ represents an acyl group having 2 to 30 carbon atoms which can contain a hydroxyl group, comprising adding water to a lipid composition comprising (A) the ceramide, (B) a long-chain fatty acid having 12 to 24 carbon atoms and (C) a nonionic surface active agent.

(8) A skin-care cosmetic comprising 0.01 to 100% by weight of the clear aqueous composition as set forth in any one of (1) to (6) above.

(9) A hair-care cosmetic comprising 0.01 to 50% by weight of the clear aqueous composition as set forth in any one of (1) to (6) above.

(10) A bath agent comprising 0.01 to 50% by weight of the clear aqueous composition as set forth in any one of (1) to (6) above.

(11) A lipid composition for preparing a clear aqueous ceramide composition, the lipid composition comprising (A) a ceramide represented by formula (I), (B) a long-chain fatty acid having 12 to 24 carbon atoms, and (C) a nonionic surface active agent, wherein the weight ratio of component (A) to component (B) is from 20:1 to 1:3, and the weight ratio of component (A) to component (C) is from 1:1 to 1:10.

DETAILED DESCRIPTION OF THE INVENTION

The ceramide which can be used as component (A) of the clear aqueous composition or the lipid composition of the present invention is represented by formula (I):

wherein $R_1$ and $R_2$ are as defined above.

The ceramides represented by formula (I) are known compounds that are either recovered from extracts of mammal tissues such as the skin of humans and pigs, the brain of cattle, and red blood cells, or extracts of plants such as soybeans and wheat, or synthesized by known processes (e.g., JP-A-7-165690, Shapiro et al., J. Am. Chem. Soc., vol. 80, p. 2170 (1958)). From the standpoint of purity, synthetic products are preferred.

In formula (I), $R_1$ represents a hydrocarbon group having 9 to 17 carbon atoms, such as nonanyl, decanyl, undecanyl, dodecanyl, tridecanyl, tetradecanyl, pentadecanyl, hexadecanyl, and heptadecanyl. $R_1$ is preferably undecanayl, dodecanyl, tridecanyl, tetradecanyl, pentadecanyl, hexadecanyl or heptadecanyl.

$R_2$ represents an acyl group having 2 to 30 carbon atoms which may have a hydroxyl group. Examples of $R_2$ are acetyl, propanoyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, oleoyl, linoleoyl, linolenoyl, nonadecanoyl, eicosanoyl, heneicosanoyl, docosanoyl, tricosanoyl, tetracosanoyl, pentacosanoyl, hexacosanoyl, heptacosanoyl, octacosanoyl, nonacosanoyl, triacontanoyl, 2-hydroxyacetyl, 2-hydroxypropanoyl, 2-hydroxybutanoyl, 2-hydroxypentanoyl, 2-hydroxyhexanoyl, 2-hydroxyheptanoyl, 2-hydroxyoctanoyl, 2-hydroxynonanoyl, 2-hydroxydecanoyl, 2-hydroxyundecanoyl, 2-hydroxydodecanoyl, 2-hydroxytridecanoyl, 2-hydroxytetradecanoyl, 2-hydroxypentadecanoyl, 2-hydroxyhexadecanoyl, 2-hydroxyheptadecanoyl, 2-hydroxyoctadecanoyl, 2-hydroxynonadecanoyl, 2-hydroxyeicosanoyl, 2-hydroxyheneicosanoyl, 2-hydroxydocosanoyl, 2-hydroxytricosanoyl, 2-hydroxytetracosanoyl, 2-hydroxypentacosanoyl, 2-hydroxyhexacosanoyl, 2-hydroxyheptacosanoyl, 2-hydroxyoctacosanoyl, 2-hydroxynonacosanoyl, 2-hydroxytriacontanoyl, 3-hydroxypropanoyl, 3-hydroxybutanoyl, 3-hydroxypentanoyl, 3-hydroxyhexanoyl, 3-hydroxyheptanoyl, 3-hydroxyoctanoyl, 3-hydroxynonanoyl, 3-hydroxydecanoyl, 3-hydroxyundecanoyl, 3-hydroxydodecanoyl, 3-hydroxytridecanoyl, 3-hydroxytetradecanoyl, 3-hydroxypentadecanoyl, 3-hydroxyhexadecanoyl, 3-hydroxyheptadecanoyl, 3-hydroxyoctadecanoyl, 3-hydroxynonadecanoyl, 3-hydroxyeicosanoyl, 3-hydroxyheneicosanoyl, 3-hydroxydocosanoyl, 3-hydroxytricosanoyl, 3-hydroxytetracosanoyl, 3-hydroxypentacosanoyl, 3-hydroxyhexacosanoyl, 3-hydroxyheptacosanoyl, 3-hydroxyoctacosanoyl, 3-hydroxynonacosanoyl, and 3-hydroxytriacontanoyl groups. $R_2$ is preferably an acyl group containing 14 to 30 carbon atoms which may have a hydroxyl group, such as a tetradecanoyl, pentadecanoyl, hexadecanoyl, heptadecanoyl, octadecanoyl, oleoyl, linoleoyl, linolenoyl, nonadecanoyl, eicosanoyl, heneicosanoyl, docosanoyl, tricosanoyl, tetracosanoyl, pentacosanoyl, hexacosanoyl, heptacosanoyl, octacosanoyl, nonacosanoyl, triacontanoyl, 2-hydroxytetradecanoyl, 2-hydroxypentadecanoyl, 2-hydroxyhexadecanoyl, 2-hydroxyheptadecanoyl, 2-hydroxyoctadecanoyl, 2-hydroxynonadecanoyl, 2-hydroxyeicosanoyl, 2-hydroxyheneicosanoyl, 2-hydroxydocosanoyl, 2-hydroxytricosanoyl, 2-hydroxytetracosanoyl, 2-hydroxypentacosanoyl, 2-hydroxyhexacosanoyl, 2-hydroxyheptacosanoyl, 2-hydroxyoctacosanoyl, 2-hydroxynonacosanoyl, 2-hydroxytriacontanoyl, 3-hydroxytetradecanoyl, 3-hydroxypentadecanoyl, 3-hydroxyhexadecanoyl, 3-hydroxyheptadecanoyl, 3-hydroxyoctadecanoyl, 3-hydroxynonadecanoyl, 3-hydroxyeicosanoyl, 3-hydroxyheneicosanoyl, 3-hydroxydocosanoyl, 3-hydroxytricosanoyl, 3-hydroxytetracosanoyl, 3-hydroxypentacosanoyl, 3-hydroxyhexacosanoyl, 3-hydroxyheptacosanoyl, 3-hydroxyoctacosanoyl, 3-hydroxynonacosanoyl, or 3-hydroxytriacontanoyl group. $R_2$ still preferably includes acyl groups such as tetradecanoyl, pentadecanoyl, hexadecanoyl, heptadecanoyl, octadecanoyl, nonadecanoyl, eicosanoyl, heneicosanoyl, docosanoyl, tricosanoyl and tetracosanoyl group; and these acyl groups with part of their hydrogen atoms displaced with a hydroxyl group. Of the hydroxyl-containing acyl groups particularly preferred is a 2-hydroxyhexadecanoyl group.

The compounds represented by formula (I) specifically include, but are not limited to, 2-tetradecanoylaminooctadecane-1,3-diol, 2-hexadecanoylaminooctadecane-1,3-diol, 2-octadecanoylaminooctadecane-1,3-diol, 2-eicosanoylaminooctadecane-1,3-diol, 2-oleoylaminooctadecane-1,3-diol, 2-linoleoylaminooctadecane-1,3-diol, 2-(2-hydroxyhexadecanoyl)aminooctadecane-1,3-diol, 2-(3-hydroxyhexadecanoyl)aminooctadecane-1,3-diol, 2-tetradecanoylaminohexadecane-1,3-diol, 2-hexadecanoylaminohexadecane-1,3-diol, 2-octadecanoylaminohexadecane-1,3-diol, 2-eicosanoylaminohexadecane-1,3-diol, 2-oleoylaminohexadecane-1,3-diol, 2-linoleoylaminohexadecane-1,3-diol, and 2-(2-hydroxyhexadecanoyl)aminohexadecane-1,3-diol.

Of the compounds represented by formula (I) particularly preferred are optically active ceramides of natural type which are represented by formula (II):

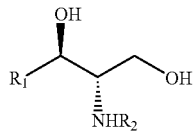

(II)

wherein $R_1$ and $R_2$ are as defined above.

Preference for the groups represented by $R_1$ and $R_2$ in formula (II) are the same as for formula (I).

Specific examples of the compounds represented by formula (II) include, but are not limited to, (2S,3R)-2-tetradecanoylaminooctadecane-1,3-diol, (2S,3R)-2-hexadecanoylaminooctadecane-1,3-diol, (2S,3R)-2-octadecanoylaminooctadecane-1,3-diol, (2S,3R)-2-nonadecanoylaminooctadecane-1,3-diol, (2S,3R)-2-eicosanoylaminooctadecane-1,3-diol, (2S,3R)-2-oleoylaminooctadecane-1,3-diol, (2S,3R)-2-linoleoylaminooctadecane-1,3-diol, (2S,3R)-2-(2-hydroxyhexadecanoyl)aminooctadecane-1,3-diol, (2S,3R)-2-(3-hydroxyhexadecanoyl)aminooctadecane-1,3-diol, (2S,3R)-2-tetradecanoylaminohexadecane-1,3-diol, (2S,3R)-2-hexadecanoylamiohexadecane-1,3-diol, (2S,3R)-2-octadecanoylaminohexadecane-1,3-diol, (2S,3R)-2-nonadecanoylaminohexadecane-1,3-diol, (2S,3R)-2-eicosanoylaminohexadecane-1,3-diol, (2S,3R)-2-oleoylaminohexadecane-1,3-diol, (2S,3R)-2-linoleoylaminohexadecane-1,3-diol, and (2S,3R)-2-(2-hydroxyhexadecanoyl)aminohexadecane-1,3-diol. These compounds can be used either individually or as a combination of two or more thereof.

The compounds of formula (II) are also known and can be prepared by known processes (e.g., JP-A-9-235259 and JP-A-6-80617).

The long-chain fatty acids having 12 to 24 carbon atoms which can be used in the invention as component (B) include lauric acid, myristic acid, palmitic acid, stearic acid, oleic acid, 12-hydroxystearic acid, tolic acid, isostearic acid, linoleic acid, linoleinic acid, eicosapentaenoic acid, and docosahexaenoic acid (DHA). They can be used either individually or as a combination of two or more thereof. Preferred of them are isostearic acid and oleic acid. Isostearic acid is particularly preferred. These fatty acids are all known compounds and commercially available.

The nonionic surface active agents which can be used as component (C) include hydrophilic ones and lipophilic ones.

Useful lipophilic nonionic surface active agents include sorbitan fatty acid esters, such as sorbitan monooleate, sorbitan monoisostearate, sorbitan monolaurate, sorbitan monopalmitate, sorbitan monostearate, sorbitan sesquioleate, sorbitan trioleate, diglycerolsorbitan penta (2-ethylhexylate), and diglycerolsorbitan tetra (2-ethylhexylate); glycerol fatty acid esters, such as cotton seed oil fatty acid monoglyceride, glycerol monoelicate, glycerol monosesquioleate, glycerol monostearate, glycerol α,α'-oleate pyroglutamate, and glycerol monoisostearate; propylene glycol fatty acid esters, such as propylene glycol monostearate; hydrogenated castor oil derivatives; and glycerol alkyl ethers.

Useful hydrophilic nonionic surface active agents include polyoxyethylene (hereinafter "POE") sorbitan fatty acid esters, such as POE-sorbitan monooleate, POE-sorbitan monostearate, POE-sorbitan monooleate, and POE-sorbitan tetraoleate; POE sorbitol fattyacidesters, such as POE-sorbitol monolaurate, POE-sorbitol monooleate, POE-sorbitol pentaoleate, and POE-sorbitol monostearate; POE glycerol fatty acid esters, such as POE-glycerol monostearate, POE-glycerol monoisostearate, and POE-glycerol triisostearate; POE fatty acid esters, such as POE monooleate, POE distearate, POE dioleate, and ethylene glycol stearate; POE alkyl ethers, such as POE lauryl ether, POE oleyl ether, POE stearyl ether, POE behenyl ether, POE 2-octyldodecyl ether, and POE cholestanol ether; POE alkylphenyl ethers, such as POE octylphenyl ether, PE nonylphenyl ether, and POE dinonylphenyl ether; POE.polyoxypropylene (hereinafter "POP") alkyl ethers; such as POE.POP cetyl ether, POE.POP 2-decyltetradecyl ether, POE.POP monobutyl ether, POE-.POP hydrogenated lanolin, POE.POP glycerol ether; tetra-POE.tetraPOP ethylenediamine condensates, such as Tetronic (RTM); POE (hydrogenated) castor oil derivatives, such as POE castor oil, POE hydrogenated castor oil, POE hydrogenated castor oil monoisostearate, POE hydrogenated castor oil triisostearate, POE hydrogenated castor oil monopyroglutamate monoisostearate, and POE hydrogenated castor oil maleate; POE molasses.lanolin derivatives, such as POE sorbitol molasses; alkanolamides, such as coconut oil fatty acid diethanolamide, lauric acid monoethanolamide, and a fatty acid isopropanolamide; polyglycerol fatty acid esters, POE propylene glycol fatty acid esters, POE alkylamines, POE fatty acid amides, sucrose fatty acid esters, POE nonylphenyl formaldehyde condensates, alkylethoxydimethylamine oxides, and trioleylphosphoric acid.

These nonionic surface active agents can be used either individually or as a combination of two or more thereof. Of the above-enumerated nonionic surface active agents preferred are POE hydrogenated castor oil derivatives and POE castor oil derivatives from the standpoint of stability and safety.

The above-described nonionic surface active agents are all known and commercially available.

Water as component (D) which constitutes the clear aqueous composition of the invention is preferably purified water prepared in a usual manner.

In the clear aqueous composition containing the ceramide in a concentration of 1.0 to 5.0% by weight, the weight ratio of the ceramide (A) to the long-chain fatty acid (B), A:B, is preferably 20:1 to 1:3. With the weight ratio of component (B) to component (A) being less than 5%, the temperature range in which the composition can maintain clearness tends to be narrowed. When component (B) is more than three times as much as the weight of component (A), the initial and sustained stability of the system tends to be deteriorated. The weight ratio of the ceramide (A) to the nonionic surface active agent (C), A:C, is preferably 1:1 to 1:10. Where component (C) is less than component (A) in weight, the composition, when formulated into preparations such as cosmetics, tends to have a narrower temperature range in which it can keep clear. It would be a false economy to use more than 10 times component (C) as much as component (A) in weight because no further improvement in system stability results. Moreover, preparations such as cosmetics containing such a large quantity of component (C) tend to have poor spreadability or uncomfortable stickiness on application.

The clear aqueous composition of the present invention can further comprise at least one compound selected from the group consisting of (E) a sterol compound and (F) a polyhydric alcohol.

Any alcohol having a steroid skeleton can be used as the sterol compound (E). Examples of suitable sterol compounds are cholesterol, dihydrocholesterol, lanosterol, dihydrolanosterol, sitosterol, and ergosterol, with cholesterol being preferred.

The polyhydric alcohol (F) includes dihydric alcohols, such as ethylene glycol, propylene glycol, trimethylene glycol, isoprene glycol, 1,2-butylene glycol, 1,3-butylene glycol, tetramethylene glycol, 2,3-butylene glycol, pentamethylene glycol, 2-butene-1,4-diol, hexylene glycol, and octylene glycol; trihydric alcohols, such as glycerol, trimethylolpropane, and 1,2,6-hexanetriol; tetrahydric alcohols, such as pentaerythritol; pentahydric alcohols, such as xylitol; hexahydric alcohols, such as sorbitol and mannitol; polyhydric alcohol polymers, such as diethylene glycol, dipropylene glycol, triethylene glycol, polypropylene glycol, tetraethylene glycol, diglycerol, polyethylene glycol, triglycerol, tetraglycerol, and polyglycerol; ethylene glycol alkyl ethers, such as ethylene glycol monomethyl ether, ethylene glycol monoethyl ether, ethylene glycol monobutyl ether, ethylene glycol monophenyl ether, ethylene glycol monohexyl ether, ethylene glycol mono(2-methylhexyl) ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether; polyethylene glycol alkyl ethers, such as diethylene glycol monobutyl ether, diethylene glycol dimethyl ether, diethylene glycol diethyl ether, diethylene glycol butyl ether, diethylene glycol methyl ethyl ether, triethylene glycol monomethyl ether, and triethylene glycol monoethyl ether; propylene glycol alkyl ethers, such as propylene glycol monomethyl ether, propylene glycol monoethyl ether, propylene glycol monobutyl ether, and propylene glycol isopropyl ether; dipropylene glycol alkyl ethers, such as dipropylene glycol methyl ether, dipropylene glycol ethyl ether, and dipropylene glycol butyl ether; dihydric alcohol ether esters, such as ethylene glycol monomethyl ether acetate, ethylene glycol monoethyl ether acetate, ethylene glycol monobutyl ether acetate, ethylene glycol monophenyl ether acetate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate; glycerol monoalkyl ethers, such as chimyl alcohol, selachyl alcohol, and batyl alcohol; dihydric alcohol diesters, such as ethylene glycol diadipate and ethylene glycol disuccinate; sugar alcohols, such as sorbitol, maltitol, maltotriose, mannitol, sucrose, erythritol, glucose, fructose, starch sugar, maltose, xylitose, and starch sugar reduction products; glysolid, tetrahydrofurfuryl alcohol, POE tetrahydrofurfuryl alcohol, POP butyl ether, POP.POE butyl ether, tripolyoxypropylene glycerol ether, POP glycerol ether, POP glycerol etherphosphate, and POP.POE pentaerythritol ether. These polyhydric alcohols can be used either individually or as a combination of two or more thereof. Of the above-listed polyhydric alcohols preferred are 1,3-butylene glycol and glycerol.

The clear aqueous composition of the invention can further contain (G) an anionic surface active agent. Useful anionic surface active agents include fatty acid soaps, such as soap base, sodium laurate, and sodium palmitate; higher alkylsulfuric ester salts, such as sodium lauryl sulfate and potassium lauryl sulfate; alkyl ether sulfuric ester salts, such as triethanolamine POE lauryl sulfate and sodium POE lauryl sulfate; N-acylsarcosinic acid salts, such as sodium lauroylsarcocinate; higher fatty acid amidosulfonates, such as sodium N-myristoyl-N-methyltaurinate, sodium methyltaurid cocoate, and sodium laurylmethyltaurid; phosphoric ester salts, such as sodium POE oleyl ether phosphate and POE stearyl ether phosphate; sulfosuccinic acid salts, such as sodium di-2-ethylhexylsulfosuccinate, sodium monolauroyl-monoethanolamide polyoxyethylene sulfosuccinate, and sodium lauryl polypropylene glycol sulfosuccinate; alkylbenzenesulfonates, such as sodium linear dodecylbenzenesulfonate and triethanolamine linear dodecylbenzenesulfonate; N-acylglutamic acid salts, such as monosodium N-lauroylglutamate, disodium N-stearoylglutamate, and monosodium N-myristoyl-L-glutamate; higher fatty acid ester sulfuric ester salts, such as sodium glycerol hydrogenated cocoate sulfate; sulfated oils, such as Turkey red oil; POE alkyl ether carboxylic acids, POE alkyl allyl ether carboxylic acid salts, α-olefinsulfonic acid salts, higher fatty acid ester sulfonic acid salts, secondary alcohol sulfuric ester salts, higher fatty acid alkylolamidosulfuric ester salts, sodium lauroyl monoethanolamidosuccinate, ditriethanolamine N-palmitoylaspartate, and sodium caseinate.

These anionic surface active agents can be used either individually or as a combination of two or more thereof. Preferred of the above-enumerated anionic surface active agents are POE phosphoric ester salts and POE alkyl allyl ether carboxylic acid salts from the standpoint of stability and safety.

The amounts of the sterol compound (E), the polyhydric alcohol (F), and the anionic surface active agent (G) which are optionally added are not particularly limited and can be decided arbitrarily in relation to the other constituent components. In a preferred embodiment, the sterol compound (E) is used in an amount of 0.001 to 3 times the weight of the ceramide (A), the polyhydric alcohol (F) is used in an amount of 0.1 to 70% by weight based on the total composition, and the anionic surface active agent (G) is used in an amount of 0.001 to 20% by weight based on the total preparation.

The clear aqueous ceramide composition of the present invention is obtained by mixing water into a lipid composition comprising the above-described components (A), (B) and (C) as essential components and, if desired, at least one compound selected from the group consisting of components (E) and (F). In a preferred embodiment, a lipid mixture is melted by heating beforehand, and previously heated water is added thereto, followed by allowing the resulting mixture to cool to room temperature. Still preferably, a lipid mixture comprising components (A), (B) and (C) and, if desired, component (E) is melted by heating, and component (F) having been heated to approximately the same temperature as the molten mixture is added thereto. Finally, water having been heated to approximately the same temperature as the mixture is added, and the resulting mixture is allowed to cool to room temperature to obtain a clear composition excellent in stability and feel on use.

In a highly preferred embodiment of the invention, the clear aqueous ceramide composition comprises a lipid composition comprising the ceramide (A), isostearic acid and/or oleic acid as component (B), and at least one of POE hydrogenated castor oil (or a derivative thereof), POE castor oil (or a derivative thereof), and a POE sorbitan fatty acid ester as component (C) and water (D). This composition sustains clearness and feels comfortable on application. Further, a composition comprising the anionic surface active agent (G) and at least one of the sterol compound (E) and the polyhydric alcohol (F) in addition to the above components is excellent in clearness and feel on use. Cholesterol is preferred as the sterol compound, and 1,3-butylene glycol or glycerol is preferred as the polyhydric alcohol.

The lipid composition which can be used for preparing the clear aqueous composition containing 1.0 to 5.0% by weight of the ceramide preferably comprises (A) a ceramide represented by formula (I), (B) a long-chain fatty acid having 12 to 24 carbon atoms, and (C) a nonionic surface active agent, the weight ratio of component (A) to component (B) being from 20:1 to 1:3, and the weight ratio of component (A) to component (C) being from 1:1 to 1:10.

The clear aqueous composition of the present invention can furthermore contain, in addition to components (A) to (G), other components commonly employed in cosmetics, external preparations for the skin, especially for medical use, bath agents, and the like. Components that could be added include, for example, powders, liquid fats and oils, solid fats and oils, waxes, hydrocarbons, higher alcohols, esters, silicone, cationic surface active agents, amphoteric surface active agents, humectants, water-soluble polymers, thickeners, film forming agents, UV-absorbers, sequestering agents, lower alcohols, sugars, amino acids, organic amino acids, synthetic resin emulsions, pH adjusting agents, dermal nutrients, vitamins, antioxidants, antioxidizing assistants, perfumes, water, and so forth.

Containing a ceramide in a high concentration, the clear aqueous composition according to the present invention can be applied as such as, for example, beauty preparations for preventing wrinkling around eyes, external preparations for the skin, skin protective preparations, and particularly medical external preparations for the treatment or protection of the skin. Further, the aqueous clear composition of the invention can be used as a material for making up cosmetics, bath agents, hair-care cosmetics, external preparations for the skin, skin protective preparations, particularly medical external preparations for the treatment or protection of the skin.

The clear aqueous composition of the invention can be formulated into various dose forms in a conventional manner. For example, the composition can be made into clear lotions, clear solutions containing organic solvents, creams, gels, emulsions, and the like.

The present invention will now be illustrated in greater detail with reference to Examples and Comparative Examples, but it should be understood that the invention is not construed as being limited thereto.

EXAMPLES 1 TO 5

Components 1 to 6 shown in Table 1 were uniformly mixed while heating at 80 to 120° C. Components 7 to 8 which had been heated to 80 to 120° C. were mixed with the mixture of components 1 to 6 while heating to prepare a lipid composition. Component 9 (purified water) which had been heated to 80 to 100° C. was slowly added to the lipid composition and mixed uniformly to prepare aqueous compositions. The proportions shown in Table 1 are given by percent by weight, and "q.s. (quantum sufficit)" means an amount sufficient to make up 100% by weight (the same applies to other Tables hereinafter given).

The compositions thus prepared were allowed to stand at room temperature for 1 month, at 40° C. for 2 weeks, and at 5° C. for 2 weeks in this order, and the appearance was observed with the naked eye and rated A to E according to the following rating system. The results obtained are shown in Table 1.

A . . . Clear

B . . . Almost clear

C . . . Slightly white-turbid

D . . . White-turbid

E . . . Precipitates observed.

TABLE 1

| Component | Example 1 | Example 2 | Example 3 | Example 4 | Example 5 |
|---|---|---|---|---|---|
| 1. Optically active ceramide (a) * | 1.50 | 3.00 | 1.00 | 1.00 | 1.00 |
| 2. Isostearic acid | 1.50 | 2.00 | 1.00 | — | 0.50 |
| 3. Oleic acid | — | — | — | 0.50 | — |
| 4. Cholesterol | — | — | — | — | 0.50 |
| 5. POE (60) ** hydrogenated castor oil | 8.00 | 15.00 | 5.00 | 5.00 | 3.25 |
| 6. POE (20) ** sorbitan monooleate | — | — | — | — | 1.75 |
| 7. 1,3-Butylene glycol | — | 10.00 | 10.00 | 5.00 | 10.00 |
| 8. Concentrated glycerin | — | — | — | 5.00 | 10.00 |
| 9. Purified water | q.s. | q.s. | q.s. | q.s. | q.s. |
| Appearance | A | B | A | A | A |

Note:
* Optically active ceramide (a): (2S,3R)-2-Octadecanoylaminooctadecane-1,3-diol (hereinafter the same)
** The number in the parentheses indicates the number of repeating ethylene oxide units (hereinafter the same).

COMPARATIVE EXAMPLES 1 TO 3

Clear aqueous compositions were prepared from the components shown in Table 2 below in the same manner as in Examples 1 to 5. The stability of the compositions was evaluated in the same manner as in Examples 1 to 5. The results are shown in Table 2.

TABLE 2

| Component | Compara. Example 1 | Compara. Example 2 | Compara. Example 3 |
|---|---|---|---|
| 1. Optically active ceramide (a) | 2.00 | — | 1.00 |
| 2. Isostearic acid | 2.00 | 2.00 | 1.00 |
| 3. Oleic acid | — | — | — |
| 4. Cholesterol | — | 2.00 | — |
| 5. POE (60) hydrogenated castor oil | — | 6.00 | — |
| 6. POE (20) sorbitan monooleate | — | — | — |
| 7. Sodium POE (4) lauryl ether phosphate | — | 2.00 | 1.00 |
| 8. Glycerin solution containing 50% lecithin hydroxide | — | — | 20.00 |
| 9. 1,3-Butylene glycol | — | 10.00 | — |
| 10. Concentrated glycerin | — | — | 20.00 |
| 11. Purified water | q.s. | q.s. | q.s. |
| Appearance | E | C | E |

It is seen from the results in Tables 1 and 2 that the compositions of Examples 1 to 5 have excellent stability over a broad temperature range, whereas the compositions of Comparative Examples are less stable, failing to achieve satisfactory results.

EXAMPLES 6 TO 8 AND APPLICATION EXAMPLE 1

Aqueous compositions were prepared from the components shown in Table 3 below in the same manner as in Examples 1 to 5. The composition of Application Example 1 presents an example of a preparation containing an anionic surface active agent. The stability of the compositions was evaluated in the same manner as in Examples 1 to 5. The results are shown in Table 3.

TABLE 3

| Component | Example 6 | Example 7 | Example 8 | Appln. Example 1 |
|---|---|---|---|---|
| 1. Optically active ceramide (a) | 2.00 | — | 1.00 | 2.00 |
| 2. Optically active ceramide (b) * | 0.50 | 2.00 | — | — |
| 3. Racemic ceramide (c) ** | — | — | 1.00 | — |
| 4. Isostearic acid | 2.00 | 2.00 | 2.00 | 2.00 |
| 5. Cholesterol | 2.00 | 2.00 | 2.00 | 2.00 |
| 6. POE (60) hydrogenated castor oil | 8.00 | 6.00 | 8.00 | 6.00 |
| 7. Sodium POE (4) lauryl ether phosphate | — | — | — | 2.00 |
| 8. 1,3-Butylene glycol | 10.00 | 10.00 | 10.00 | 10.00 |
| 9. Purified water | q.s. | q.s. | q.s. | q.s. |
| Appearance | A | A | A | A |

Note:
* (2S,3R)-2-(2-hydroxyhexadecanoyl)aminooctadecane-1,3-diol
** 2-Octadecanoylaminooctadecane-1,3-diol From the fact that the composition of Comparative Example 2 containing no ceramide showed white turbidity whereas clear aqueous compositions were obtained in Application Example 1, which is a composition of Comparative Example 2 having a ceramide incorporated therein, and Examples 1 to 8, it is assumed that the compositions of the present invention comprise a water-soluble lipid composite essentially composed of a ceramide.

EXAMPLE 9

A lotion weighing 100 g was prepared from the components shown in Table 4 in a conventional manner. The resulting lotion was evaluated in the same manner as in Examples 1 to 5. The result is shown in Table 4.

TABLE 4

| Component | Amount (wt %) |
|---|---|
| 1. Concentrated glycerin | 3.00 |
| 2. 1,3-Butylene glycol | 5.00 |
| 3. p-Hydroxybenzoic ester | 0.20 |
| 4. Perfume | 0.01 |
| 5. Clear aqueous composition of Example 1 | 10.00 |
| 6. Purified water | q.s. |
| Appearance | A |

EXAMPLE 10

A liquid beauty preparation weighing 100 g was prepared from the components shown in Table 5 below in a conventional manner. The resulting beauty preparation was evaluated in the same manner as in Examples 1 to 5. The result is shown in Table 5.

TABLE 5

| Component | Amount (wt %) |
|---|---|
| 1. Hydroxyethyl cellulose | 0.50 |
| 2. Concentrated glycerin | 5.00 |
| 3. 1,3-Butylene glycol | 5.00 |
| 4. p-Hydroxybenzoic ester | 0.20 |
| 5. Perfume | 0.01 |
| 6. Clear aqueous composition of Example 2 | 25.00 |
| 7. Purified water | q.s. |
| Appearance | A |

EXAMPLE 11

Emollient cream weighing 100 g was prepared from the following components in a conventional manner.

| | |
|---|---|
| Hydrogenated castor oil | 6.00 wt % |
| Stearic acid | 3.00 wt % |
| Cetanol | 4.00 wt % |
| Squalane | 2.00 wt % |
| Neopentyl glycol dicaprinate | 8.00 wt % |
| POE (20) sorbitan monostearate | 4.00 wt % |
| Lipophilic glycerol monostearate | 2.30 wt % |
| Sodium stearoyl-N-methyltaurinate | 1.70 wt % |
| 1,3-Butylene glycol | 7.00 wt % |
| Concentrated glycerin | 3.00 wt % |
| p-Hydroxybenzoic ester | 0.25 wt % |
| Perfume | 0.05 wt % |
| Clear aqueous composition of Example 1 | 5.00 wt % |
| Purified water | q.s. |

EXAMPLE 12

An emollient emulsion weighing 100 g was prepared from the following components in a conventional manner.

| | |
|---|---|
| Stearic acid | 1.00 wt % |
| Cholesteryl isostearate | 2.00 wt % |
| Jojoba oil | 4.00 wt % |

-continued

| | |
|---|---|
| Squalane | 8.00 wt % |
| Sorbitan sesquioleate | 0.80 wt % |
| POE (20) sorbitan monostearate | 1.20 wt % |
| 1,3-Butylene glycol | 5.00 wt % |
| p-Hydroxybenzoic ester | 0.25 wt % |
| L-Arginine | 0.40 wt % |
| Carboxyvinyl polymer | 0.20 wt % |
| Perfume | 0.05 wt % |
| Clear aqueous composition of Example 6 | 5.00 wt % |
| Purified water | q.s. |

EXAMPLE 13

A conditioning shampoo weighing 100 g was prepared from the following components in a conventional manner.

| | |
|---|---|
| Sodium POE lauryl ether sulfate | 14.00 wt % |
| Laurylamidopropylbetaine | 4.00 wt % |
| Coconut oil fatty acid diethanolamide | 3.00 wt % |
| Cationic cellulose | 0.50 wt % |
| Ethylene glycol distearate | 1.00 wt % |
| p-Hydroxybenzoic ester | 0.25 wt % |
| Citric acid | adequate amount |
| Perfume | 0.50 wt % |
| Clear aqueous composition of Example 6 | 5.00 wt % |
| Purified water | q.s. |

EXAMPLE 14

A hair rinse weighing 100 g was prepared from the following components in a conventional manner.

| | |
|---|---|
| Stearyltrimethylammonium chloride | 1.00 wt % |
| Cetanol | 3.00 wt % |
| Polymethylsiloxane | 1.00 wt % |
| POE stearyl ether | 1.00 wt % |
| Propylene glycol | 5.00 wt % |
| p-Hydroxybenzoic ester | 0.25 wt % |
| Sodium hydroxide | adequate amount |
| Citric acid | adequate amount |
| Perfume | 0.50 wt % |
| Clear aqueous composition of Example 7 | 5.00 wt % |
| Purified water | q.s. |

EXAMPLE 15

A hair conditioner weighing 100 g was prepared from the following components in a conventional manner.

| | |
|---|---|
| Stearyltrimethylammonium chloride | 0.50 wt % |
| Distearyldimethylammonium chloride | 1.50 wt % |
| Jojoba oil | 2.50 wt % |
| Cetanol | 4.50 wt % |
| Liquid lanolin | 2.00 wt % |
| POE stearyl ether | 1.50 wt % |
| Concentrated glycerin | 7.00 wt % |
| p-Hydroxybenzoic ester | 0.25 wt % |
| Sodium hydroxide | adequate amount |
| Citric acid | adequate amount |
| Perfume | 0.50 wt % |
| Clear aqueous composition of Example 6 | 5.00 wt % |
| Purified water | q.s. |

EXAMPLE 16

A hair tonic weighing 100 g was prepared from the following components in a conventional manner.

| | |
|---|---|
| Swertia extract | 2.00 wt % |
| L-Menthol | 0.10 wt % |
| Hinokitiol | 0.01 wt % |
| Perfume | 0.10 wt % |
| p-Hydroxybenzoic ester | 0.20 wt % |
| POE hydrogenated castor oil | 0.50 wt % |
| Clear aqueous composition of Example 4 | 5.00 wt % |
| Purified water | q.s. |

EXAMPLE 17

A hair blow lotion weighing 100 g was prepared from the following components in a conventional manner.

| | |
|---|---|
| POE · POP butyl ether | 0.50 wt % |
| Polyvinylpyrrolidone | 2.50 wt % |
| Stearyltrimethylammonium chloride | 4.50 wt % |
| Polyether-modified silicone | 2.00 wt % |
| p-Hydroxybenzoic ester | 0.20 wt % |
| Citric acid | adequate amount |
| Perfume | 0.10 wt % |
| Clear aqueous composition of Example 3 | 5.00 wt % |
| Purified water | q.s. |

EXAMPLE 18

A liquid bath agent weighing 100 g was prepared from the following components in a usual manner.

| | |
|---|---|
| Dipropylene glycol | 50.00 wt % |
| 1,3-Butylene glycol | 10.00 wt % |
| p-Hydroxybenzoic ester | 0.20 wt % |
| Perfume | 1.00 wt % |
| Clear aqueous composition of Example 5 | 5.00 wt % |
| Purified water | q.s. |

The ceramide-containing lipid composition according to the present invention exhibits excellent compatibility with water, and the aqueous composition prepared therefrom and having a ceramide content of 1.0 to 5.0% by weight is clear or almost clear and excellent in stability, safety and feel on use. In particular, the clear aqueous composition of the present invention is not only stable when allowed to stand at room temperature but maintains clearness even when left to stand in high or low temperature. Additionally the composition of the invention keeps the clear state even when diluted with water to an arbitrary concentration.

The clear aqueous composition of the invention having these excellent effects is useful as cosmetics, bath agents, hair-care products, external preparations for the skin, skin protective preparations, particularly medical external preparations for the treatment or protection of the skin, or a component making up these preparations. The composition of the invention is effective for protection and treatment of the skin and especially suited for use in cosmetics or pharmaceuticals.

While the invention has been described in detail and with reference to specific embodiments thereof, it will be apparent to one skilled in the art that various changes and modifications can be made therein without departing from the spirit and scope thereof.

This application is based on Japanese patent application No. 2000-138072 filed on May 11, 2000, the entire contents of which incorporated herein by reference.

What is claimed is:

1. A method of preparing a clear aqueous cosmetic additive composition suitable for use in cosmetics, said composition being free of an ionic surface active agent, being not irritating to the skin, and consisting essentially of 1.0 to 5.0% by weight of a ceramide represented by formula (I):

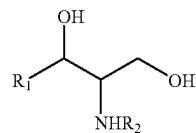

(I)

wherein $R_1$ represents a hydrocarbon group selected from the group consisting of nonanyl, decanyl, undecanyl, dodecanyl, tridecanyl, tetradecanyl, pentadecanyl, hexadecanyl, heptadecanyl and octadecanyl; and $R_2$ represents a substituted acyl group having 14 to 30 carbon atoms wherein the substituent on $R_2$ is a hydroxyl group, optionally in combination with a ceramide of formula (III)

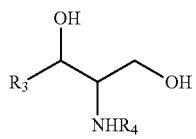

(III)

wherein $R_3$ represents a hydrocarbon group selected from the group consisting of nonanyl, decanyl, undecanyl, dodecanyl, tridecanyl, tetradecanyl, pentadecanyl, hexadecanyl, and heptadecanyl; and $R_4$ represents an acyl group having 2 to 30 carbon atoms which can contain a hydroxyl group, said method comprising:
forming a lipid composition consisting essentially of (A) said ceramide, (B) a long-chain fatty acid having 12 to 24 carbon atoms, and (C) a nonionic lipophilic or hydrophilic surface active agent, and (E) optionally a sterol compound, wherein components (A), (B), (C) and optionally (E) are uniformly mixed while heating at 80 to 120° C. to accomplish said forming form the lipid composition;

and then adding (F) a polyhydric alcohol which has been heated to 80 to 120° C. to the lipid composition and mixing components (A), (B), (C) and optionally (E) with the (F) polyhydric alcohol while heating; and thereafter further adding water which has been heated to 80 to 100° C.; and then permitting the resulting mixture to cool to room temperature.

2. The method of claim 1, wherein said ceramide represented by formula (I) is an optically active ceramide of natural type represented by formula (II):

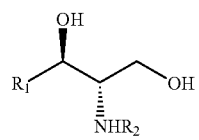

(II)

optionally in combination with a ceramide of formula (IV)

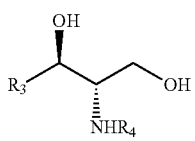

(IV)

wherein $R_1$, $R_2$, $R_3$ and $R_4$ are as defined in claim 1.

3. The method of claim 2, wherein the non-ionic surface active agent is a polyoxyethylene hydrogenated castor oil.

4. The method of claim 2, wherein cholesterol is further added to the water and the lipid composition.

5. The method of claim 2, wherein the long-chain fatty acid is at least one of isostearic acid and oleic acid.

6. The method of claim 2, wherein the long-chain fatty acid is isostearic acid and oleic acid in combination.

7. The method of claim 6, wherein the non-ionic surface active agent is a polyoxyethylene hydrogenated castor oil and wherein cholesterol is further added to the water and the lipid composition.

8. The method of claim 2, wherein the compound represented by formula (II) is selected from the group consisting of:
(2S, 3R)-2-(2-hydroxyhexadecanoyl) aminooctadecane-1,3-diol,
(2S,3R)-2-(3-hydroxyhexadecanoyl) aminooctadecane-1,3-diol, and
(2S,3R)-2-(2-hydroxyhexadecanoyl)aminohexadecane-1,3-diol.

9. The method according to claim 2, wherein the compound of formula (IV) is (2S, 3R)-2-octadecanoylaminooctadecane-1,3-diol.

10. The method according to claim 7, wherein the compound of formula (IV) is (2S, 3R)-2-octadecanoylaminooctadecane-1,3-diol.

11. The method of claim 2, wherein the compound of formula (II) is (2S, 3R)-2-(2-hydroxyhexadecanoyl) aminooctadecane-1,3-diol.

12. The method of claim 7, wherein the compound of formula (II) is (2S, 3R)-2-(2-hydroxyhexadecanoyl) aminooctadecane-1,3-diol.

13. The method of claim 7, wherein the compound of formula (II) is (2S,3R)-2-(3-hydroxyhexadecanoyl) aminooctadecane-1,3-diol.

14. The method of claim 2, wherein the compound of formula (II) is (2S,3R)-2-(3-hydroxyhexadecanoyl) aminooctadecane-1,3-diol.

15. The method of claim 2, wherein the compound of formula (II) is (2S,3R)-2-(2hydroxyhexadecanoyl) aminohexadecane-1,3-diol.

16. The method according to claim 7, wherein the compound of formula (II) is (2S,3R)-2-(2-hydroxyhexadecanoyl) aminohexadecane-1,3-diol.

17. The method of claim 2, wherein the compound represented by formula (IV) is selected from the group consisting of:
(2S, 3R)-2-tetradecanoylaminooctadecane-1,3-diol,
(2S, 3R)-2-hexadecanoylaminooctadecane-1,3-diol,
(2S, 3R)-2-octadecanoylaminooctadecane-1,3-diol,
(2S, 3R)-2-nonadecanoylaminooctadecane-1,3-diol,
(2S, 3R)-2-eicosanoylaminooctadecane-1,3-diol,
(2S,3R)-2-oleoylaminooctadecane-1,3-diol,
(2S, 3R)-2-linoleoylaminooctadecane-1,3-diol,
(2S, 3R)-2-tetradecanoylaminohexadecane-1,3-diol,
(2S, 3R)-2-hexadecanoylamiohexadecane-1,3-diol,
(2S, 3R)-2-octadecanoylaminohexadecane-1,3-diol,
(2S, 3R)-2-nonadecanoylaminohexadecane-1,3-diol,
(2S, 3R)-2-eicosanoylaminohexadecane-1,3-diol,
(2S, 3R)-2-oleoylaminohexadecane-1,3-diol, and
(2S,3R)-2-linoleoylaminohexadecane-1,3-diol.

18. The method of claim 1, wherein the composition comprises the ceramide of formula (III).

19. The method of claim 2, wherein the composition comprises the ceramide of formula (IV).

\* \* \* \* \*